US012699096B2

(12) United States Patent
Bux et al.

(10) Patent No.: US 12,699,096 B2
(45) Date of Patent: Aug. 4, 2026

(54) METHOD OF DETECTING LUNG CANCER

(71) Applicant: BIOMARK CANCER SYSTEMS INC., Richmond (CA)

(72) Inventors: Rashid Bux, Vancouver (CA); Daniel Sitar, Winnipeg (CA)

(73) Assignee: BIOMARK CANCER SYSTEMS INC., Richmond (CA)

( * ) Notice: Subject to any disclaimer, the term of this patent is extended or adjusted under 35 U.S.C. 154(b) by 748 days.

(21) Appl. No.: 18/304,741

(22) Filed: Apr. 21, 2023

(65) Prior Publication Data

US 2023/0251261 A1     Aug. 10, 2023

Related U.S. Application Data

(63) Continuation of application No. 15/739,608, filed as application No. PCT/CA2016/050758 on Jun. 27, 2016, now Pat. No. 11,656,229.

(60) Provisional application No. 62/185,213, filed on Jun. 26, 2015.

(51) Int. Cl.
  *G01N 33/5752*     (2026.01)
  *G01N 33/68*     (2006.01)

(52) U.S. Cl.
  CPC ..... *G01N 33/5752* (2026.01); *G01N 33/6812* (2013.01); *G01N 2800/60* (2013.01)

(58) Field of Classification Search
  CPC ........... G01N 33/5752; G01N 33/6812; G01N 2800/60
  See application file for complete search history.

(56) References Cited

U.S. PATENT DOCUMENTS

| | | |
|---|---|---|
| 6,811,967 B2 | 11/2004 | Sitar et al. |
| 9,476,098 B2 | 10/2016 | Mann et al. |
| 9,664,681 B2 | 5/2017 | Imaizumi et al. |
| 2007/0178504 A1 | 8/2007 | Colpitts et al. |
| 2010/0093006 A1 | 4/2010 | Nagase et al. |
| 2011/0053156 A1 | 3/2011 | Vander Borght et al. |
| 2011/0082089 A1 | 4/2011 | Borlak et al. |
| 2012/0122243 A1 | 5/2012 | Kamlage et al. |
| 2012/0178111 A1 | 7/2012 | Diamandis et al. |
| 2012/0225954 A1 | 9/2012 | Moran et al. |
| 2015/0024399 A1 | 1/2015 | Hayes et al. |
| 2016/0195543 A1 | 7/2016 | Shah et al. |
| 2017/0160281 A1 | 6/2017 | Aghvanyan et al. |

FOREIGN PATENT DOCUMENTS

| | | |
|---|---|---|
| CA | 2808859 | 2/2012 |
| CN | 101806805 | 8/2010 |
| CN | 104678002 | 6/2015 |
| CN | 103616450 | 12/2015 |
| EP | 2605016 | 6/2013 |
| EP | 2728018 | 11/2016 |
| JP | 2006199655 | 8/2006 |
| JP | 2007119445 | 5/2007 |
| JP | 2010038796 | 2/2010 |
| JP | 2011517341 | 6/2011 |
| JP | 2011247869 | 12/2011 |
| JP | 2008164517 | 8/2012 |
| JP | 2012-233902 | 11/2012 |
| JP | 2012520463 | 2/2016 |
| WO | 2004081569 | 9/2004 |
| WO | 2007/076439 | 7/2007 |
| WO | 2011128256 | 10/2011 |
| WO | 2008/016111 | 4/2014 |
| WO | 2014072086 | 5/2014 |
| WO | 2012127984 | 7/2014 |
| WO | 2014/139025 | 9/2014 |
| WO | 2015/088947 | 6/2015 |
| WO | 2016097769 | 6/2016 |
| WO | 2016112174 | 7/2016 |
| WO | 2016205960 | 12/2016 |
| WO | 2018148600 | 8/2018 |
| WO | 2018216009 | 11/2018 |
| WO | 2020124276 | 6/2020 |
| WO | 2021016711 | 2/2021 |

OTHER PUBLICATIONS

Wu, et al., "Urinary metabolomic study of non-small cell lung carcinoma based on ultra high performance liquid chromatography coupled with quadrupole time-of-flight mass spectrometry", J. Sep. Sci., 2014, 37, pp. 1728-1735.

Birse, et al., "Blood-based lung cancer biomarkers identified through proteomic discovery in cancer tissues, cell lines and conditioned medium", Clinical Proteomics (2015) 12:18 (12 pages).

Fan, et al., "Understanding receiver operating characteristic (ROC) curves", Can J Emerg Med 2006;8(1): pp. 19-20.

Xu, et al., "Effects of smoking and smoking cessation on human serum metabolite profile: results from the KORA cohort study", BMC Medicine 2013, 11:60 (14 pages).

An, et al., "Integrated Ionization Approach for RRLC-MS/MS-based Metabonomics: Finding Potential Biomarkers for Lung Cancer", Journal of Proteome, 2010, 9, pp. 4071-4081.

Duarte, et al., "Metabolic profiling of biofluids: potential in lung cancer screening and diagnosis", Expert Rev Mol Diag, 2013, 13(7), pp. 737-748.

Li, et al., "Serum metabolic profiling study of lung cancer using ultra high performance liquid chromatography quadrupole time-of-flight mass spectrometry", Journal of Chromatography B, 2014, 966, pp. 147-153.

Li, Yaqiong, "Lung cancer serum metabonomics study based on optimized least squares-discriminant analysis and nuclear magnetic resonance spectroscopy", Dissertation, Central China Normal University, 2014.

(Continued)

*Primary Examiner* — Jeremy C Flinders

(74) *Attorney, Agent, or Firm* — Hovey Williams LLP; Crissa A. Cook

(57) ABSTRACT

A biomarker panel and method for a urine test for detecting lung cancer detects a biomarker selected from the group of biomarkers consisting of DMA, C5:1, C10:1, ADMA, C5-OH, SDMA, and kynurenine, or a combination thereof.

12 Claims, 21 Drawing Sheets

(56)     References Cited

OTHER PUBLICATIONS

Khan, et al., "Noninvasive Serum Metabolomic Profiling Reveals Elevated Kynurenine Pathway's Metabolites in Humans with Prostate Cancer", J. Proteome Res, 2019, 18, pp. 1532-1541.
International Search Report and Written Opinion in corresponding PCT/CA2016/050758, dated Sep. 20, 2016, p pages.
Wu, et al., "The application of polyamines in serum to diagnosis of lung cancer", Journal of Henan Medical University, 2000, 35(3) (abstract attached).
Marton, et al., "Measurment of putrescine, spermidine, and spermine in physiological fluids by use of an amino acid analyzer", Clin Chem, 1973, 19(8), pp. 923-926.
Carrola, et al., "Metabolic signatures of lung cancer in biofluids: NMR-based metabolmisc of urine", Journal of Proteome Research, 2011, 10, pp. 221-230.
Langsdorf, et al. (Biocrates Application Note 2001-1) (Year: 2011).
Musajo, et al. (Nature, 1955, 4463:855-856).
Soliman, et al. (J. Chromatog. A, 2012, 1267:162-169).
Dubreuil, et al. (J. Physiology, 1953, pp. 20-26).
Kobayashi, et al. (Cancer, Epidemiology, Biomarkers & Prevention, 2023, 22;571-579).
Breier, et al. (PLOS ONE, 2014, 9(2):e89728).
Bouatra, et al. (PLOS ONE, 2013, 8(9):e73076).
Laiakis, et al., (Targeted Metabolomics Using the UPLC/MS-based AbsoluteIDQ p180 Kit, 2013).
Rocha, et al. (Metabolic signature of lung cancer: a metabolomic study of human tissues and biofluids, 2014, Dissertation).
Wu, et al. (J. Sep. Sci., 2014, 37:1728-1735).
International Search Report and Written Opinion in corresponding PCT/CA2016/050758, dated Sep. 20, 2016, 9 pages.
Wu Y, et al. "The application of polyamines in serum to diagnosis of lunch cancer", J Henan Medical University, 2000, 35(03), abstract.
Marton, L. J., et al. "Measurement of Putrescine, Spermidine, and Spermine in physiological fluids by use of an amino acid analyzer" Clin Chem, 1973, 19(8), pp. 923-926.
Carrola J, et al. "Metabolic signatures of lung cancer in biofluids NMR-based metabolomisc of urine" J Proteome Research, 2011, 10, pp. 221-230.
An, et al. "Integrated ionization approach for RRLC-MS/MS-based metabonomics: finding potential biomarkers for lung cancer", J Proeteome, 9, 2010, pp. 4071-4081.
Duarte, et al. "Metabolic profiling of biofluids: potential in lung cancer screening and diagnosis" Expert Rev Mol Diagn, 2013, 13(7), pp. 737-748.
Li, et al. "Serum metabolic profiling study of lung cancer using ultra high performance liquid chromatography/ quadrupole time-of-flight mass spectrometry" J Chrom B, 2014, 966, pp. 147-153.
Li, Yaqiong, "Lung cencer serum metabonomics study based on optimized least squares-discriminant analysis and nuclear magnetic resonance spectroscopy", Dissertation, Central China Normal University, 2014, abstract.

Khan, et al (Nonivasive serum metabolomic profiling reveals elevated kynurenine pathway's metabolites in human with prostate cancer, J Proteome Res, 2019, 18, pp. 1532-1541.
Chen, et al. "Metabolomic profiling of human serum in lung cancer patients using liquid chromatography/hybrid quadrupole time-of-flight mass spectrometry and gas chromatography/mass spectrometry", J Cancer Res clin Oncol, 2015, 141, pp. 705-718 (abstract attached).
Singhal, et al., "Liquid Biopsy In Lung Cancer Screening: The Contribution of Metabolomics. Results of A Pilot Study,", Cancers (Basel), Jul. 29, 2019;11(8):1069.
Ludwig, et al., "Biomarkers In Cancer Staging, Prognosis And Treatment Selection," Nature Reviews/Cancer, Nov. 2005, 5(11), pp. 845-856 (abstract attached).
Yang, et al., "Docetaxel and Cisplatin Regimen for Non-Small-Cell Lung Cancer", Hospital Pharmacy, Jul. 9, 2013, 48(7):550-557.
Mahieu, et al., "Extension and significance testing of Variable Importance in Projection (VIP) indices in Partial Least Squares regression and Principal Components Analysis", Chem and Intel Lab Systems, Nov. 15, 2023, 242, 8 pages.
Chong, et al., "Performance of some variable selection methods when multicollinearity is present", Chemometrics and Intelligent Laboratory Systems, 2005, 78, 103-112.
He, et al., "In Situ Characterizing Membrane Lipid Phenotype of Human Lung Cancer Cell Lines Using Mass Spectrometry Profiling", Journal of Cancer, 2016, 7(7):810-6.
Yu, et al., "Next-generation metabolomics in lung cancer diagnosis, treatment and precision medicine: mini review", Oncotarget, Dec. 29, 2017, 8(70), pp. 115774-115786.
Zhang, et al., "A High-Performing Plasma Metabolite Panel for Early-Stage Lung Cancer Detection", Cancers, 2020, 12(622), 22 pages.
Xu, et al., "Effects of smoking and smoking cessation on human serum metabolite profile: results from the KORA cohort study", BMC Medicine, 2013, 11:60.
International Search Report and Written Opinion in PCT/CA2019/051908, dated Apr. 1, 2021, 14 pages.
International Search Report and Written Opinion in PCT/CA2020/051041, dated Nov. 26, 2020.
Office Action in corresponding U.S. Appl. No. 15/739,608, dated Dec. 21, 2021.
Office Action in corresponding U.S. Appl. No. 15/739,608, dated Feb. 14, 2019.
Office Action in corresponding U.S. Appl. No. 15/739,608, dated Jun. 15, 2018.
Office Action in corresponding U.S. Appl. No. 15/739,608, dated Jun. 21, 2022.
Office Action in corresponding U.S. Appl. No. 15/739,608, dated Jun. 24, 2021.
Office Action in corresponding U.S. Appl. No. 15/739,608, dated Mar. 5, 2020.
Office Action in corresponding U.S. Appl. No. 15/739,608, dated Nov. 5, 2020.

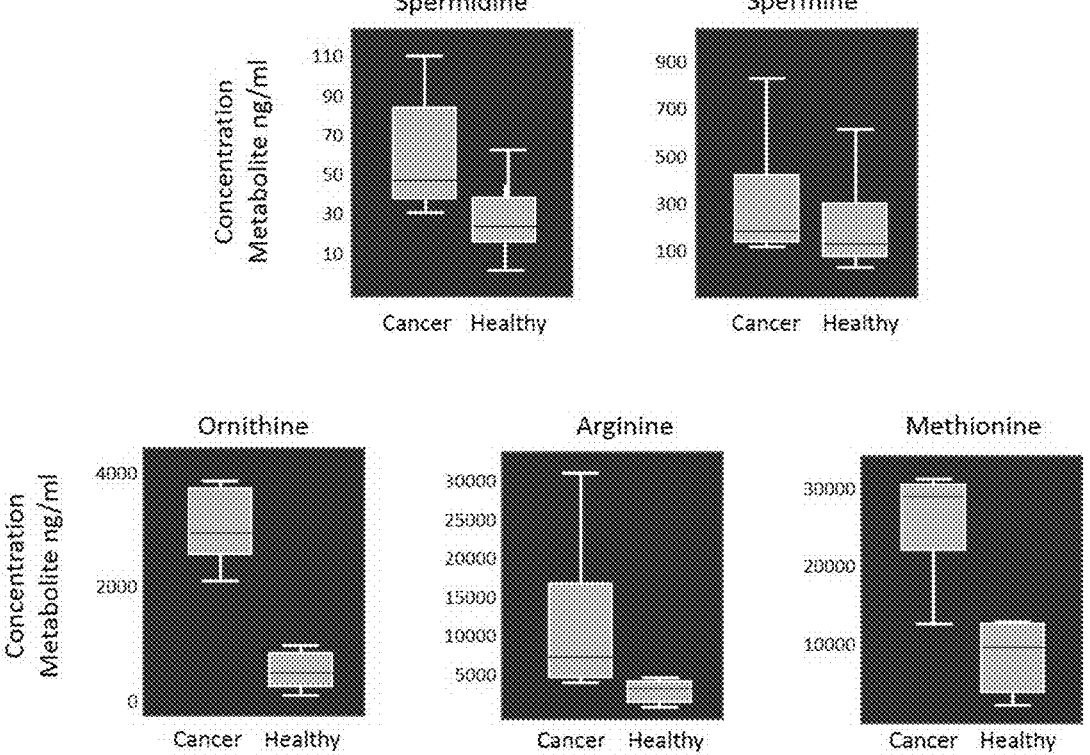
FIGURE 1: Box-and-Whiskers plots showing the concentrates of metabolites in healthy patients and cancer patients.

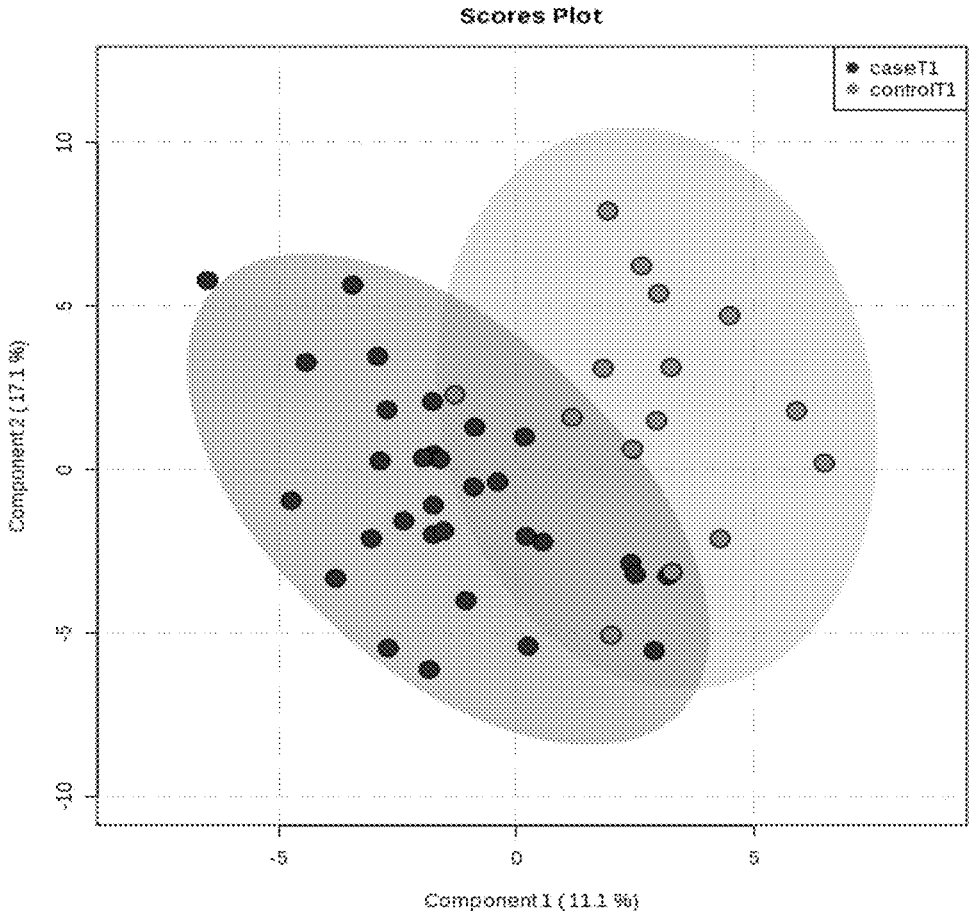
FIGURE 2: PLS-DA plot showing separation between control patients (*green*) and lung cancer patients (*red*) based on an analysis of urine samples.

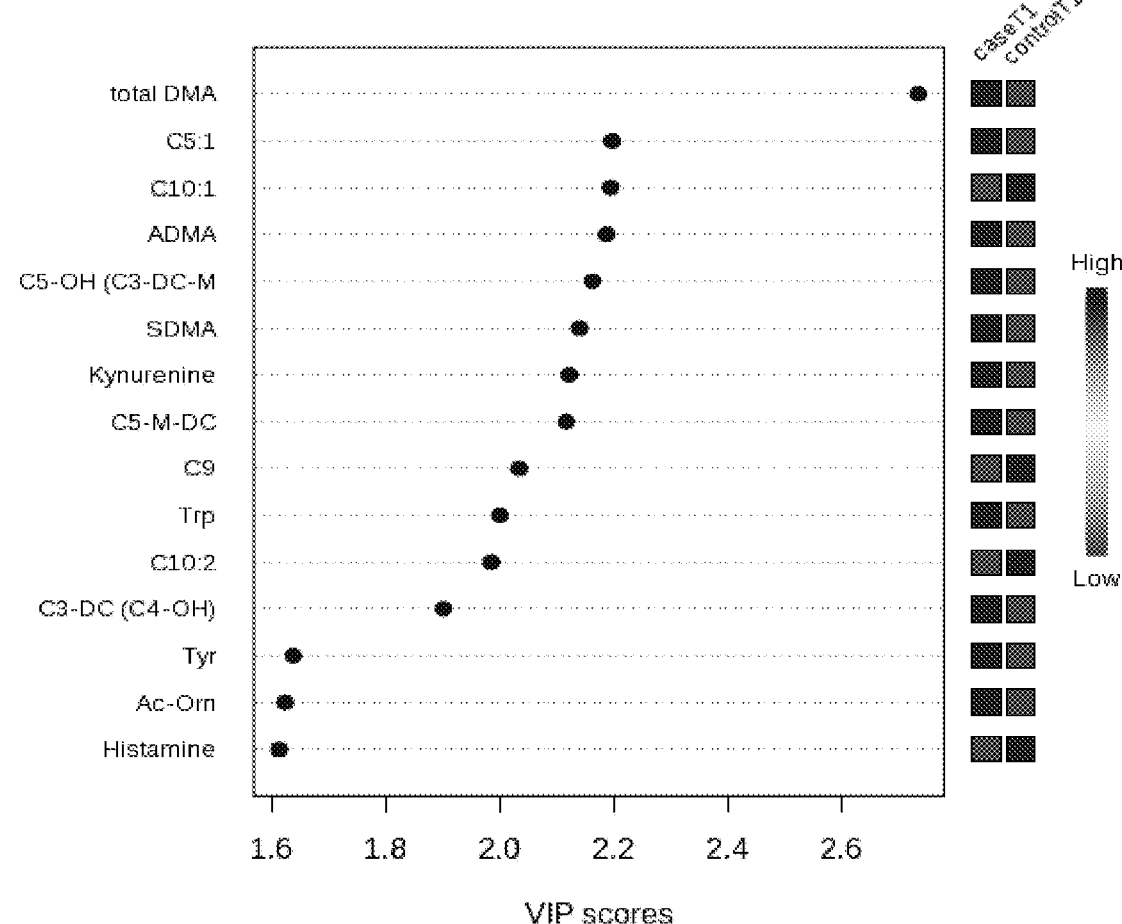
FIGURE 3: VIP analysis plot ranking discriminating urine metabolites in descending order of importance.

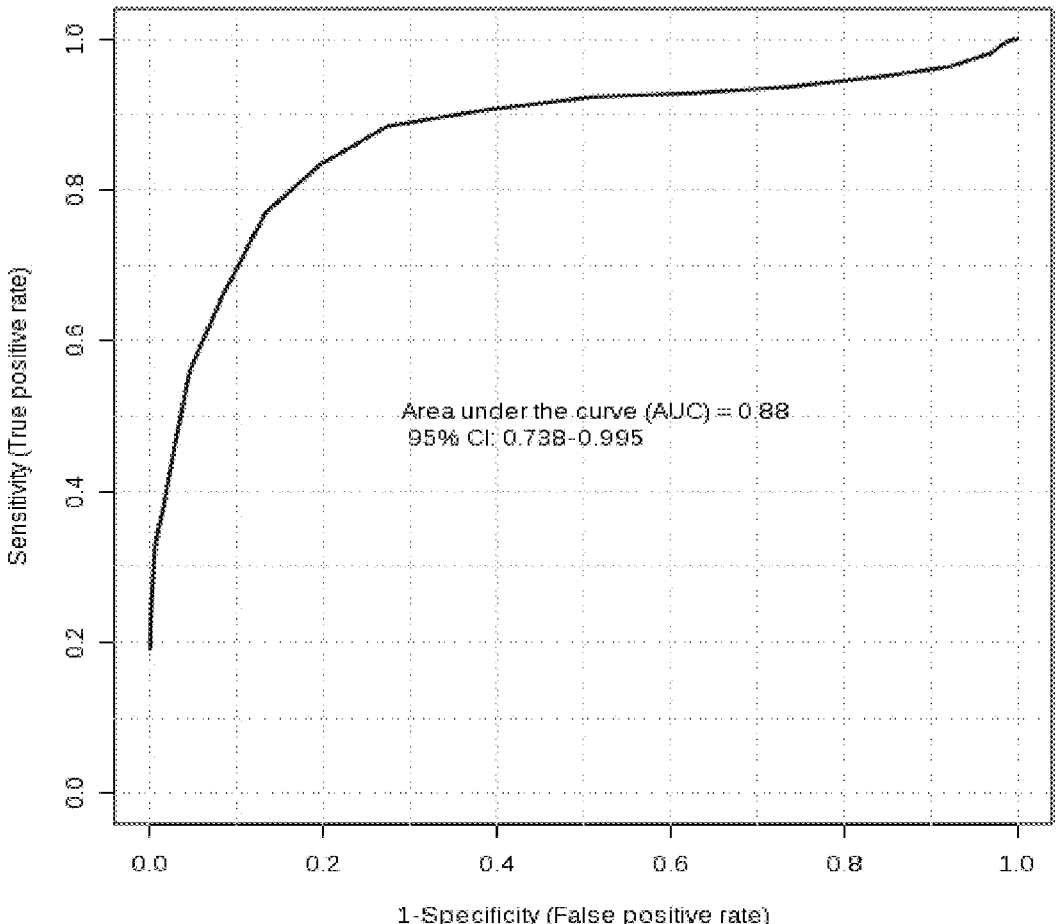
FIGURE 4: ROC analysis including the seven most important metabolites from VIP analysis of urine samples shown in Figure 3. AUC: 0.88 with a maximal sensitivity of 86.7% and specificity of 80.6%.

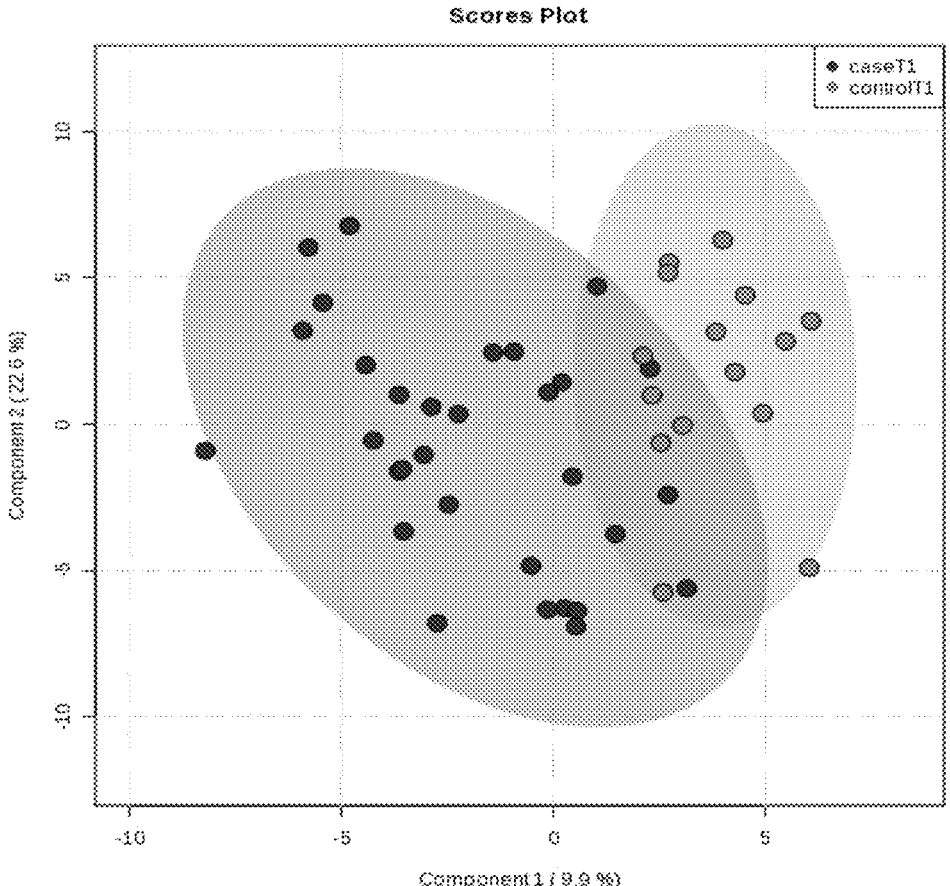
FIGURE 5: PLS-DA plot showing separation between control patients (*green*) and lung cancer patients (*red*) based on an analysis of serum samples.

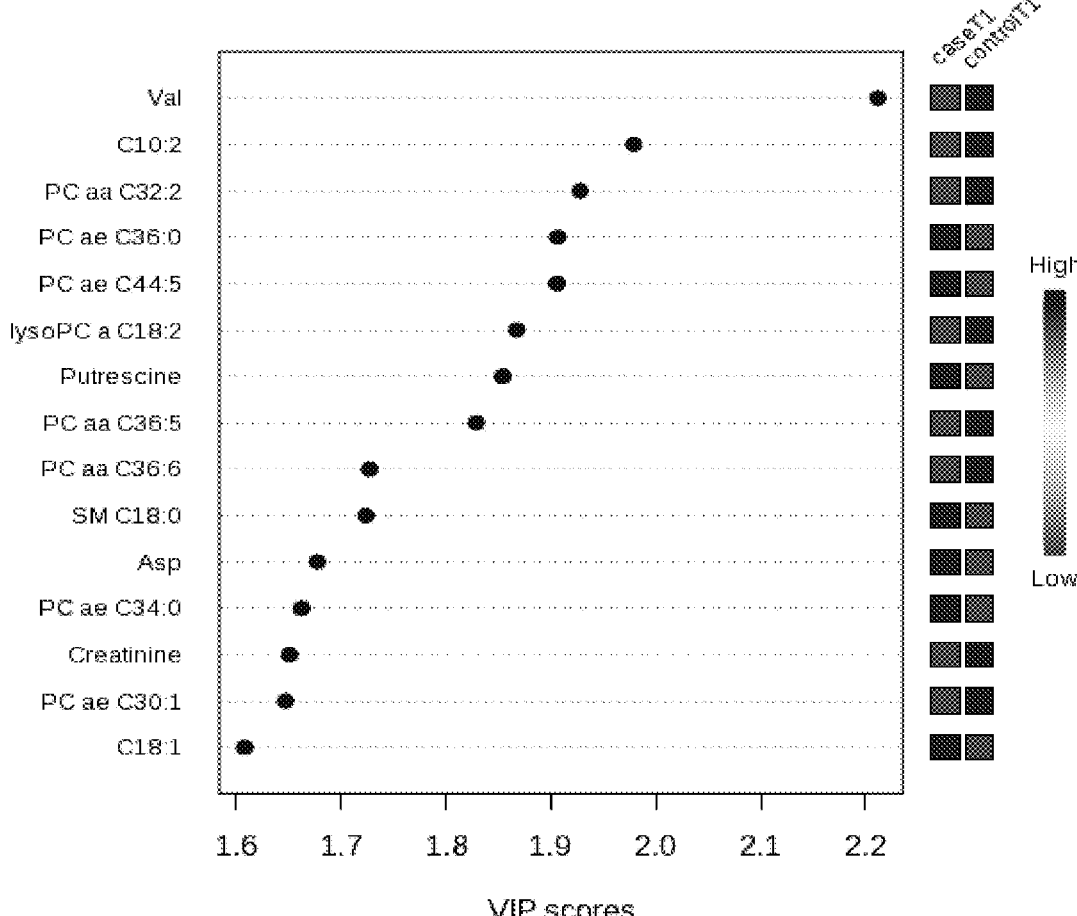
FIGURE 6: VIP analysis plot ranking discriminating serum metabolites in descending order of importance.

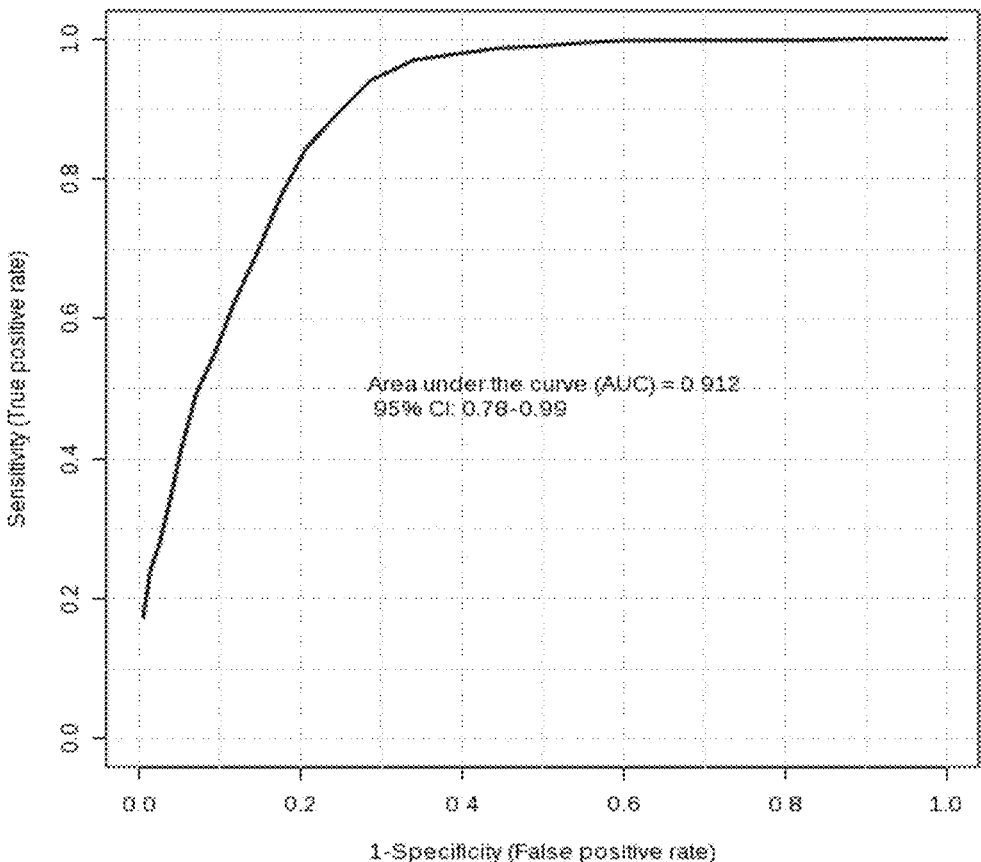
FIGURE 7: ROC analysis including the five most important metabolites from VIP analysis of serum samples shown in Figure 6. AUC: 0.9 with a maximal sensitivity of 80% and specificity of 87.1%.

| Metabolite | Mean (SD) | | p-value | q-value (FDR) | Fold Change | Case / Control |
|---|---|---|---|---|---|---|
| | Case_T1 (n=26) | Control_T1 (n=15) | | | | |
| Valine | 207.500 (51.472) | 275.867 (51.148) | 0.0002 | 0.0022 | -1.33 | Down |
| Arginine | 113.838 (56.870) | 123.507 (47.220) | $0.2911^{W}$ | 0.4002 | -1.08 | Down |
| Ornithine | 39.623 (15.068) | 42.807 (11.623) | 0.4851 | 0.5787 | -1.08 | Down |
| Methionine | 33.696 (8.907) | 34.573 (8.693) | 0.7610 | 0.7610 | -1.03 | Down |
| Spermidine | 0.248 (0.054) | 0.221 (0.020) | 0.0266 | 0.0488 | 1.12 | Up |
| Spermine | 0.308 (0.047) | 0.269 (0.021) | $0.0012^{W}$ | 0.0043 | 1.15 | Up |
| Diacetylspermine | 0.061 (0.038) | 0.036 (0.005) | $0.0006^{W}$ | 0.0031 | 1.66 | Up |
| Decadienylcarnitine (C10:2) | 0.041 (0.050) | 0.095 (0.072) | $0.0061^{W}$ | 0.0134 | -2.34 | Down |
| PC aa C32:2 | 12.162 (7.208) | 8.246 (3.932) | $0.0716^{W}$ | 0.1125 | 1.47 | Up |
| PC ae C36:0 | 2.207 (0.655) | 2.070 (0.670) | 0.5261 | 0.5787 | 1.07 | Up |
| lysoPC a C18:2 | 3.818 (2.011) | 5.691 (1.794) | 0.0049 | 0.0134 | -1.49 | Down |

FIGURE 8: Univariate Analysis of individual metabolites in a serum sample at time T1.

| Metabolite | Mean (SD) | | p-value | q-value (FDR) | Fold Change | Case / Control |
|---|---|---|---|---|---|---|
| | Case_T2 (n=26) | Control_T2 (n=15) | | | | |
| Valine | 204.615 (45.354) | 294.533 (59.346) | < 0.0001 | < 0.0001 | -1.44 | Down |
| Arginine | 116.835 (60.028) | 139.880 (54.971) | 0.0857 W | 0.1179 | -1.2 | Down |
| Ornithine | 45.942 (16.561) | 50.753 (16.650) | 0.3767 | 0.3767 | -1.1 | Down |
| Methionine | 31.442 (9.864) | 39.020 (10.199) | 0.0529 W | 0.0875 | -1.24 | Down |
| Spermidine | 0.253 (0.088) | 0.212 (0.042) | 0.1759 W | 0.2150 | 1.2 | Up |
| Spermine | 0.311 (0.059) | 0.266 (0.024) | 0.0051 W | 0.0172 | 1.17 | Up |
| Diacetylspermine | 0.061 (0.063) | 0.037 (0.005) | 0.0063 W | 0.0172 | 1.65 | Up |
| Decadienylcarnitine C102 | 0.048 (0.059) | 0.088 (0.081) | 0.0557 W | 0.0875 | -1.83 | Down |
| PC aa C322 | 12.139 (8.158) | 7.329 (2.841) | 0.0423 W | 0.0875 | 1.66 | Up |
| PC ae C360 | 2.148 (0.670) | 1.903 (0.546) | 0.2364 | 0.2600 | 1.13 | Up |
| lysoPC a C182 | 3.569 (2.091) | 5.407 (1.483) | 0.0053 W | 0.0172 | -1.51 | Down |

FIGURE 9: Univariate Analysis of individual metabolites in a serum sample at time T2.

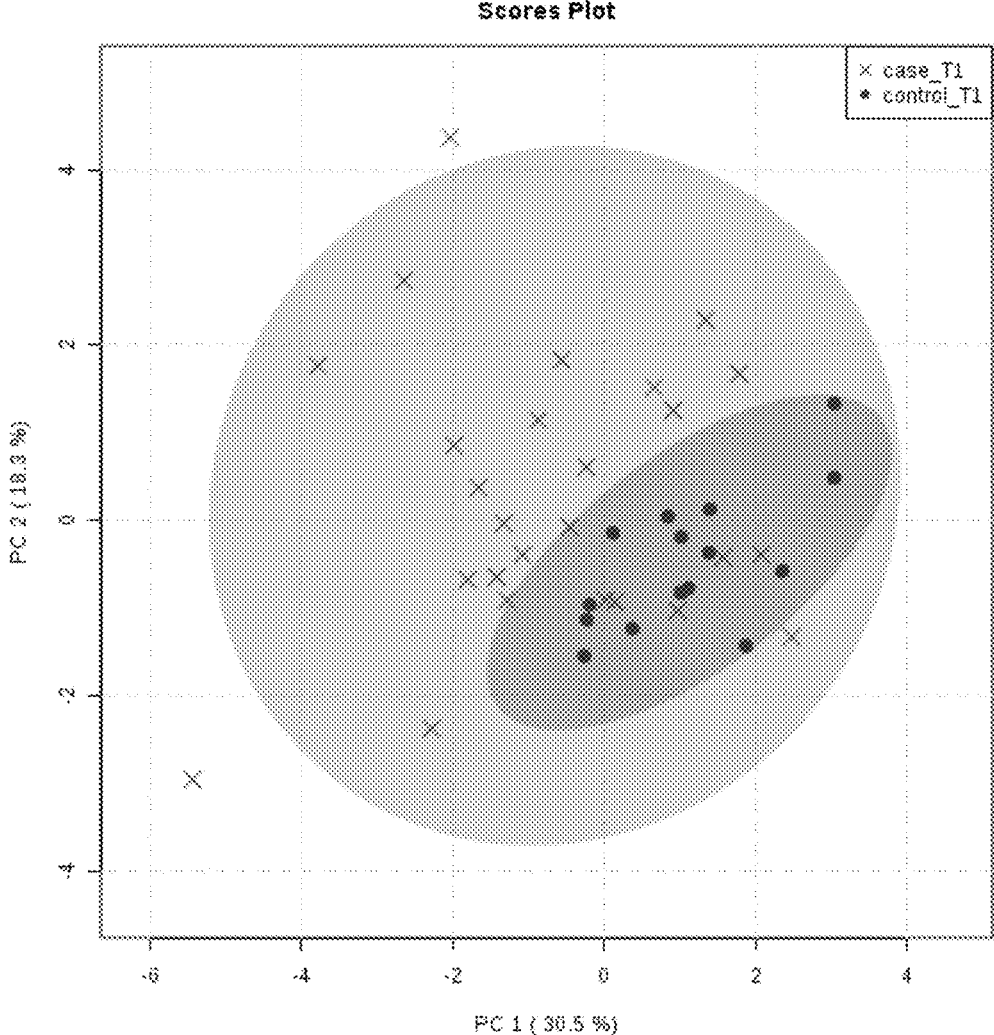
FIGURE 10: PCA plot showing separation between control patients (*blue*) and lung cancer patients (*red*) based on an analysis of serum samples at time T1.

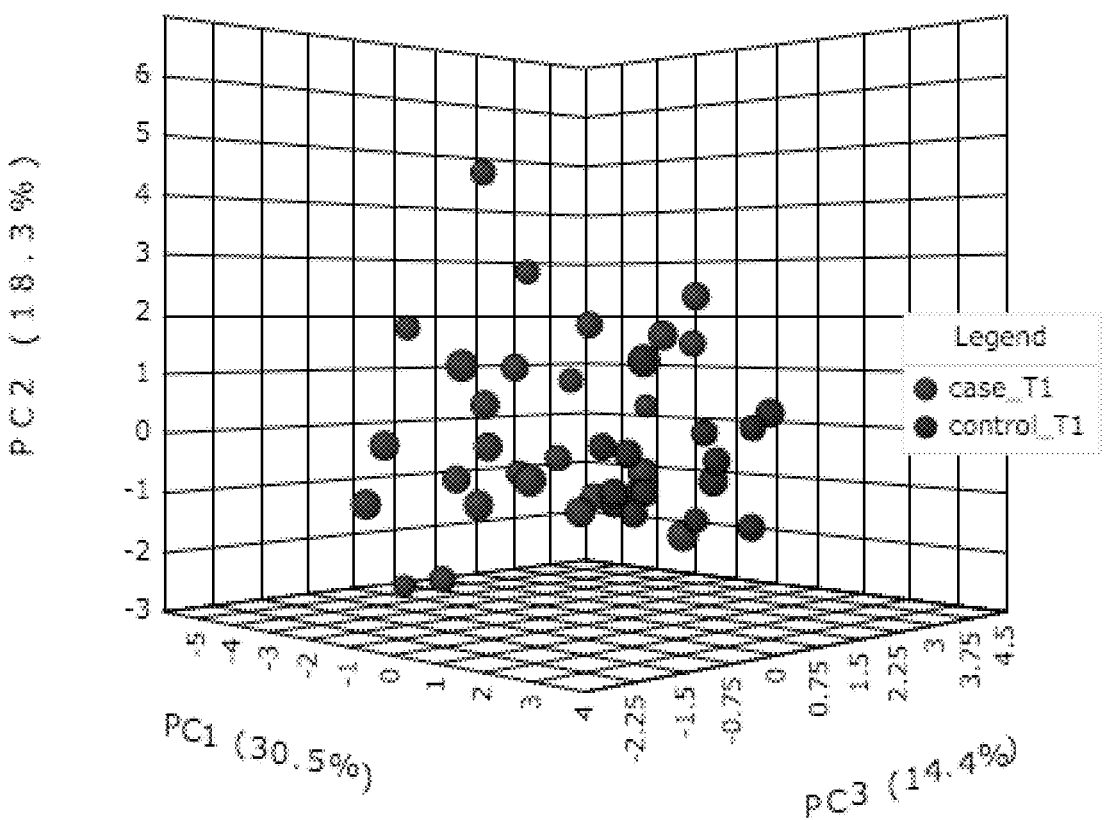
FIGURE 11: PCA plot showing separation between control patients (*blue*) and lung cancer patients (*red*) based on an analysis of serum samples at time T1.

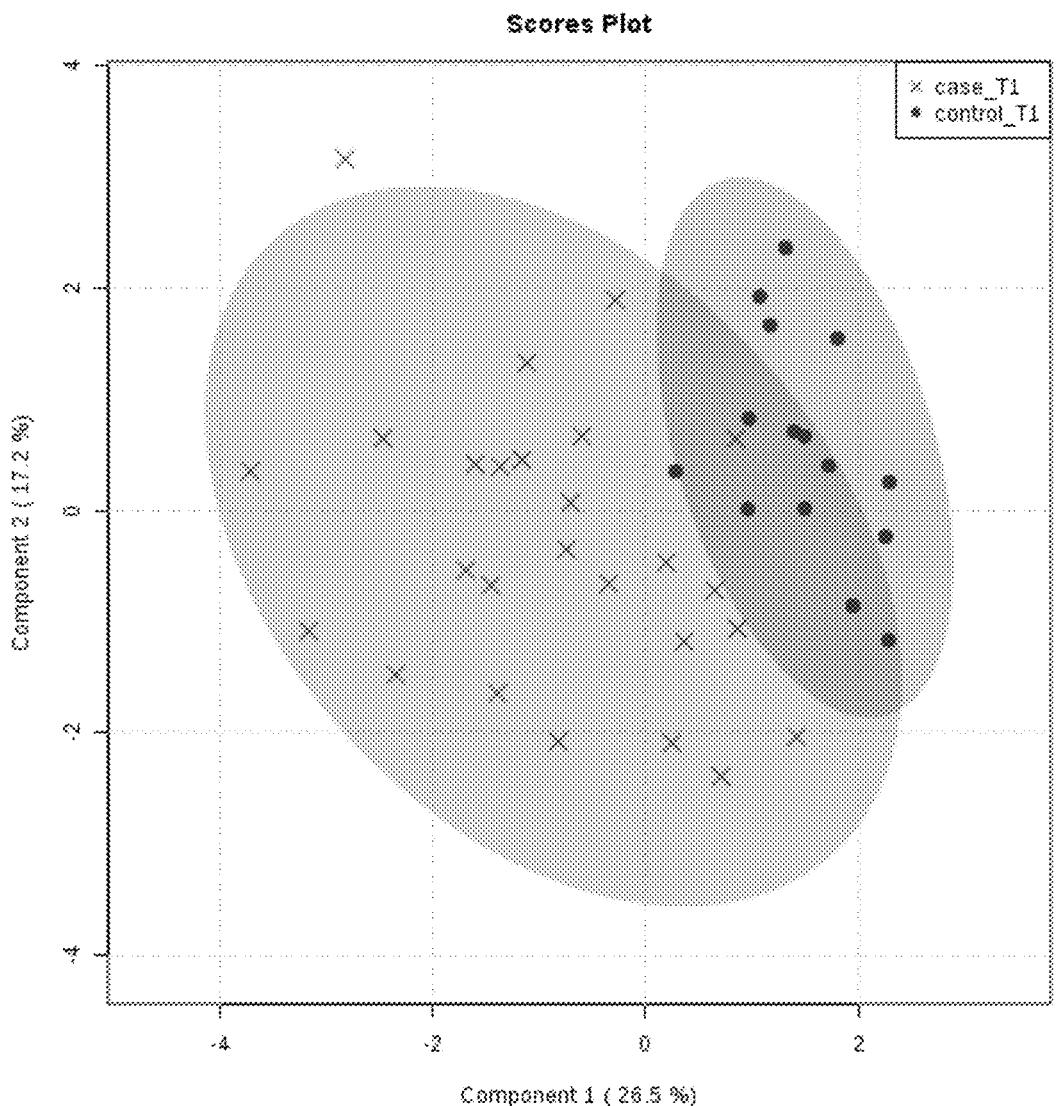
FIGURE 12: PLS-DA plot showing separation between control patients (*blue*) and lung cancer patients (*red*) based on an analysis of serum samples at time T1.

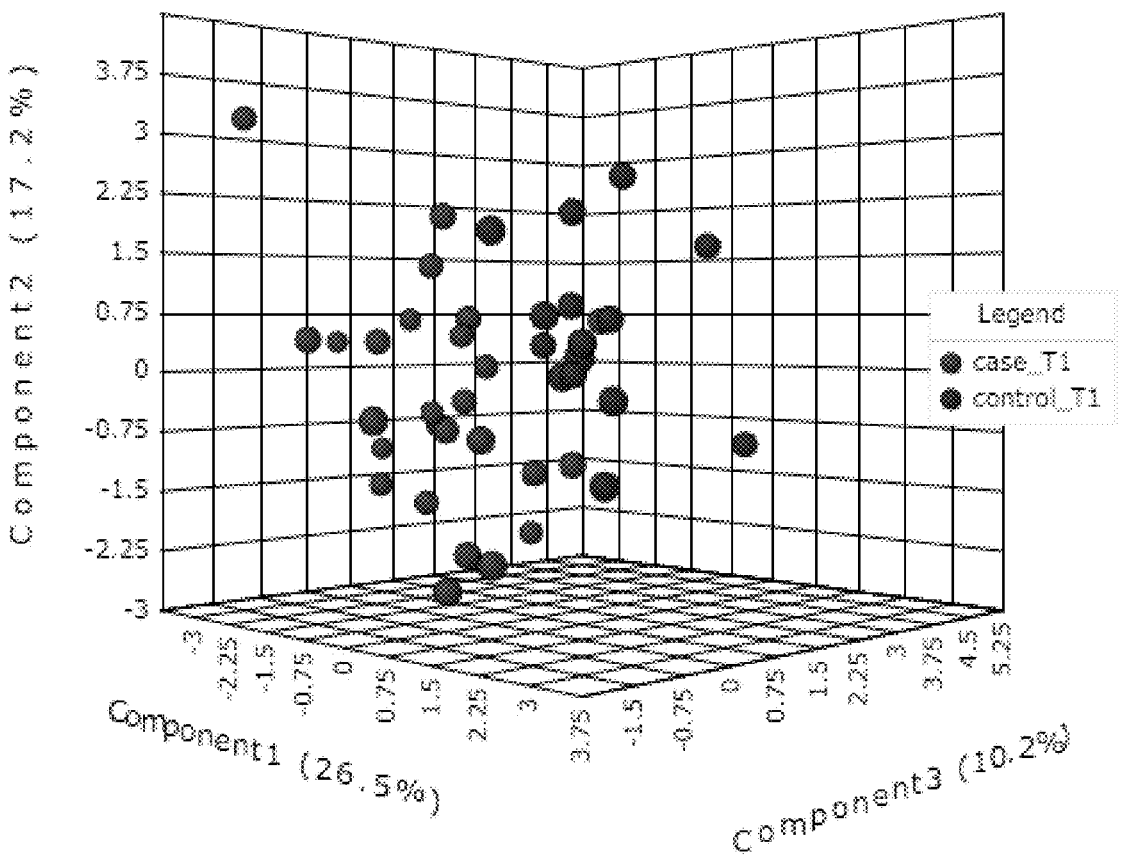
FIGURE 13: PLS-DA plot showing separation between control patients (*blue*) and lung cancer patients (*red*) based on an analysis of serum samples at time T1.

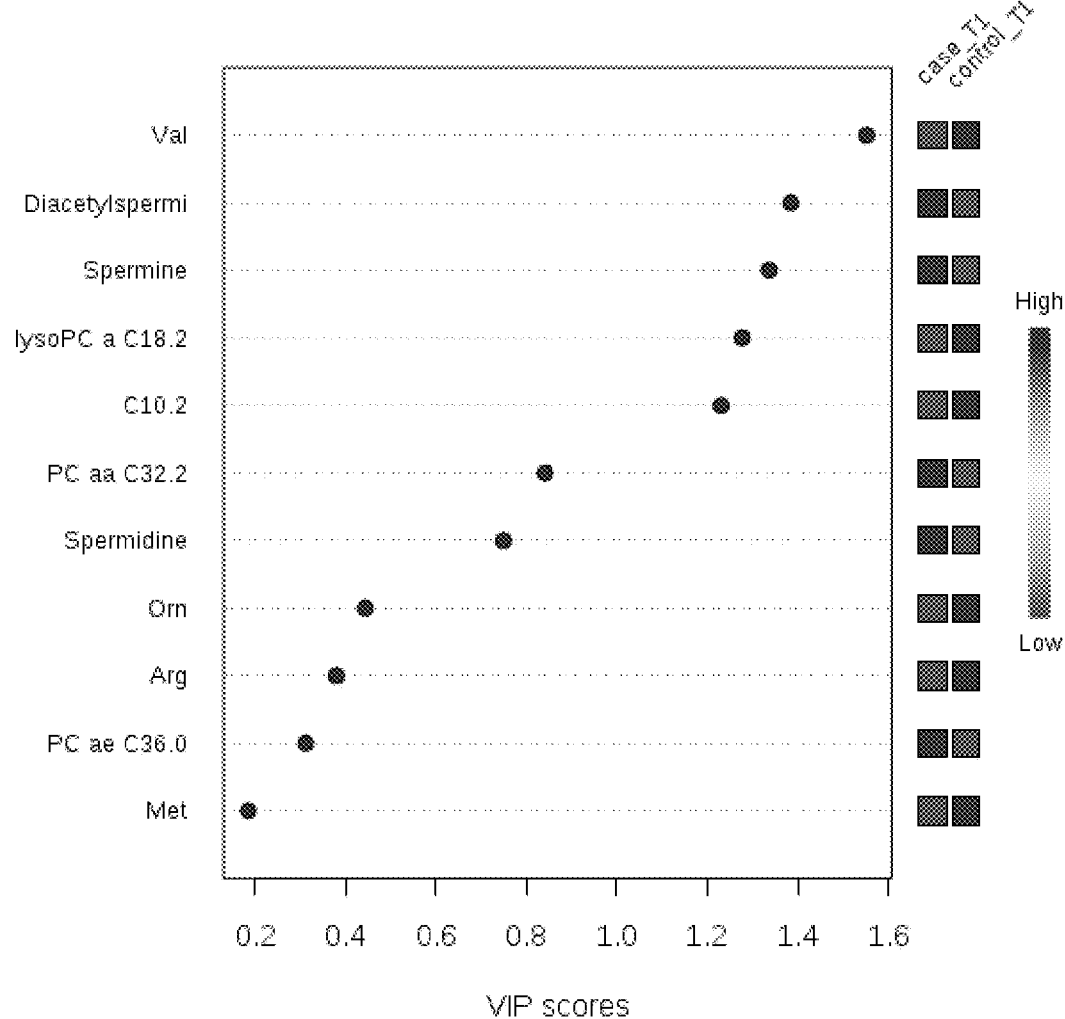
FIGURE 14: VIP analysis plot ranking discriminating serum metabolites in descending order of importance at time T1.

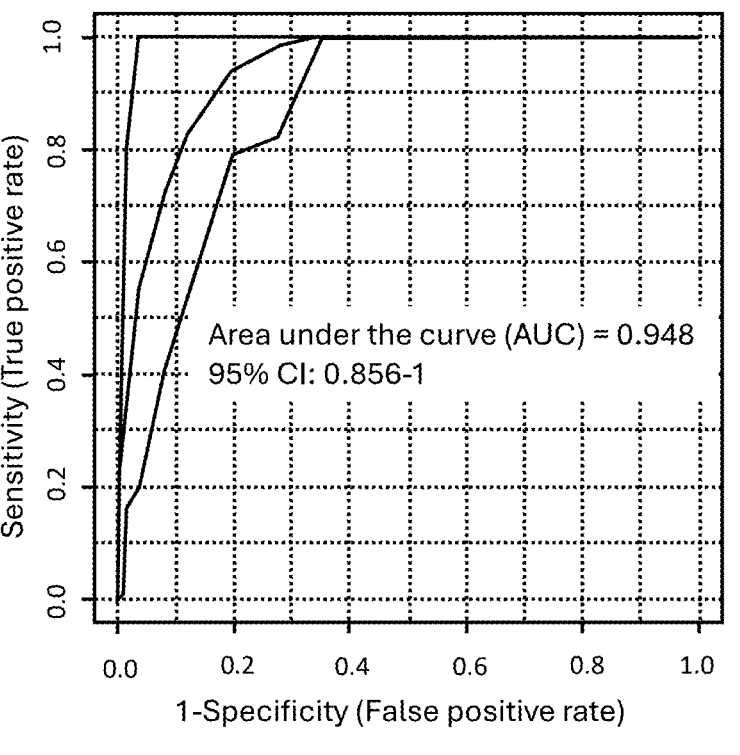
ROC Analysis (PLS-DA model)
log-Auto scale, serum all @ T1
- PLS-DA model with following metabolites:
  - Val, Diacetylspermine, Spermine, LysoPC a C18:2, C10:2
- Permutation test (1000 repeats) for ROC analysis: P-value < 0.001
FIGURE 15: ROC analysis including the five most important metabolites from the VIP analysis of serum samples shown in Figure 14.

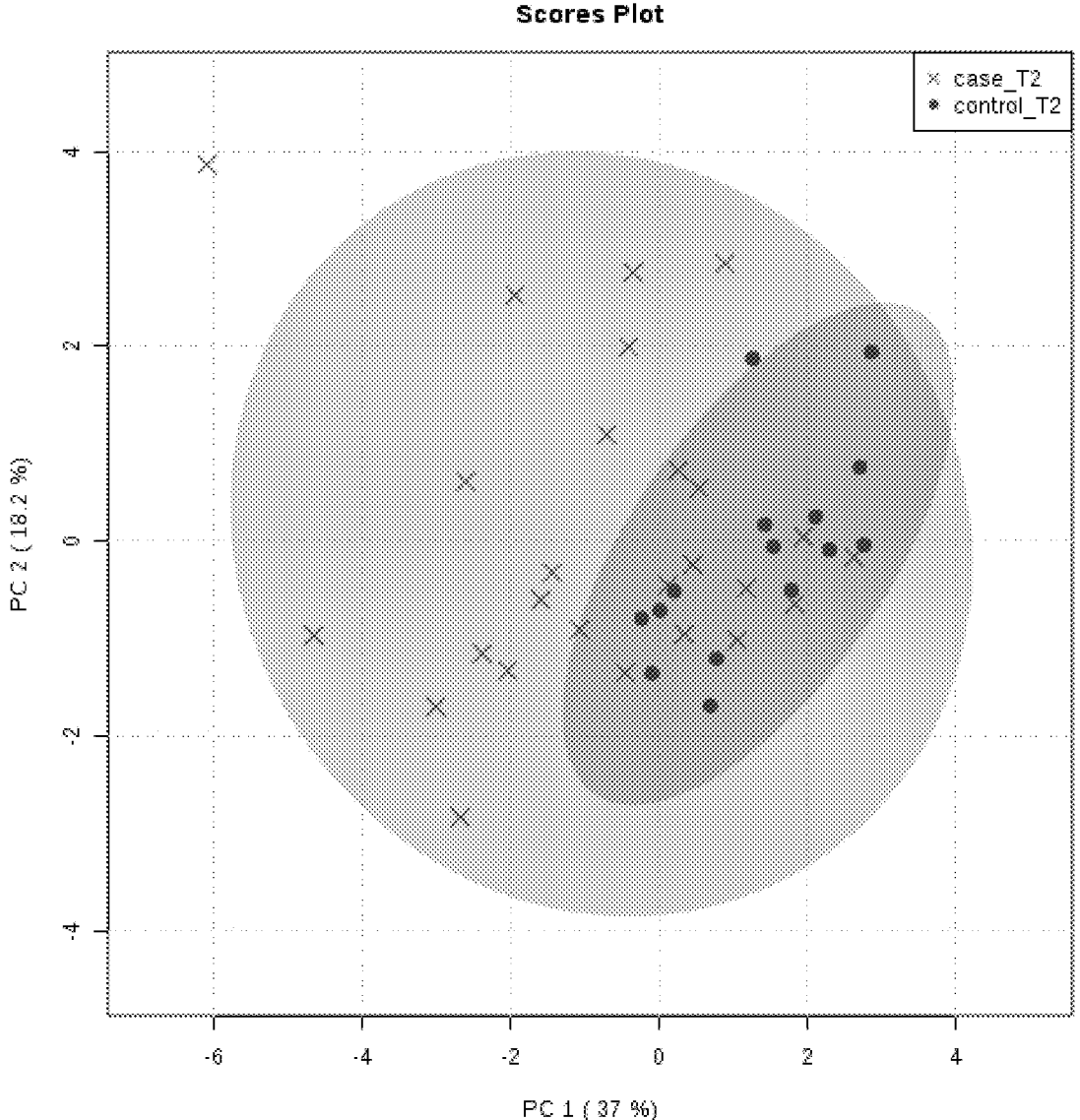
FIGURE 16: PCA plot showing separation between control patients (*blue*) and lung cancer patients (*red*) based on an analysis of serum samples at time T2.

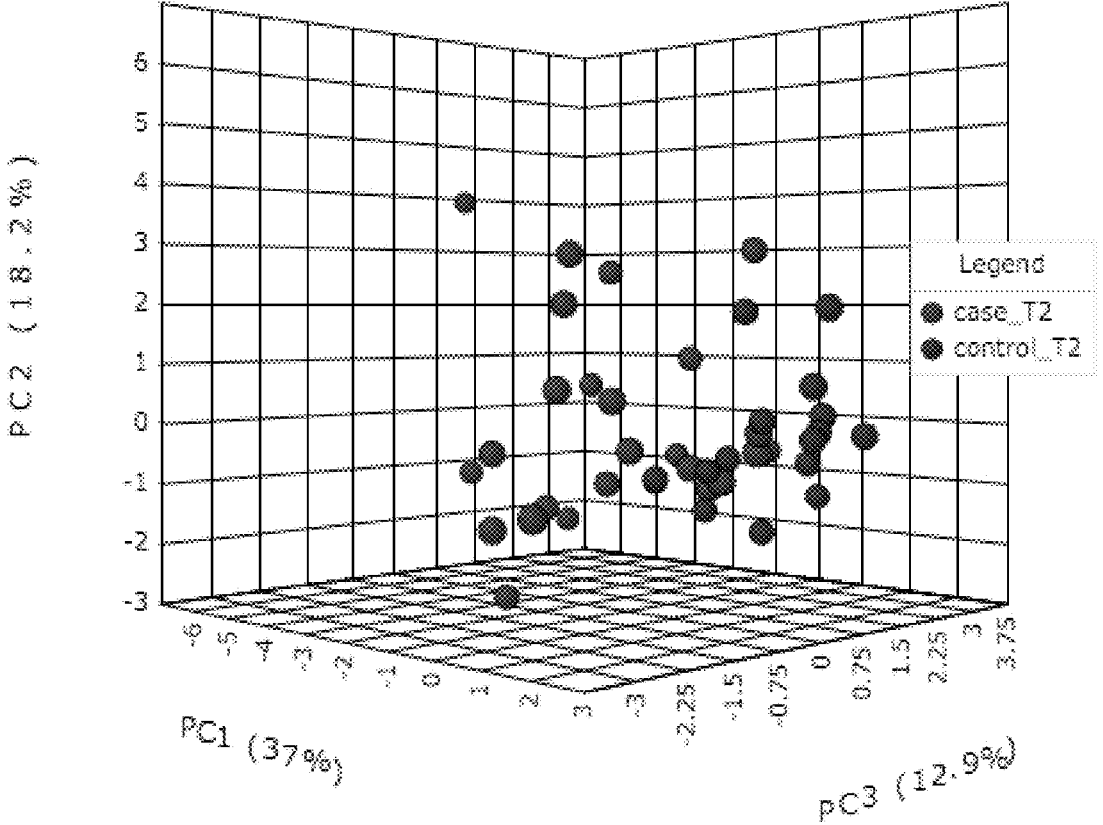
FIGURE 17: PCA plot showing separation between control patients (*blue*) and lung cancer patients (*red*) based on an analysis of serum samples at time T2.

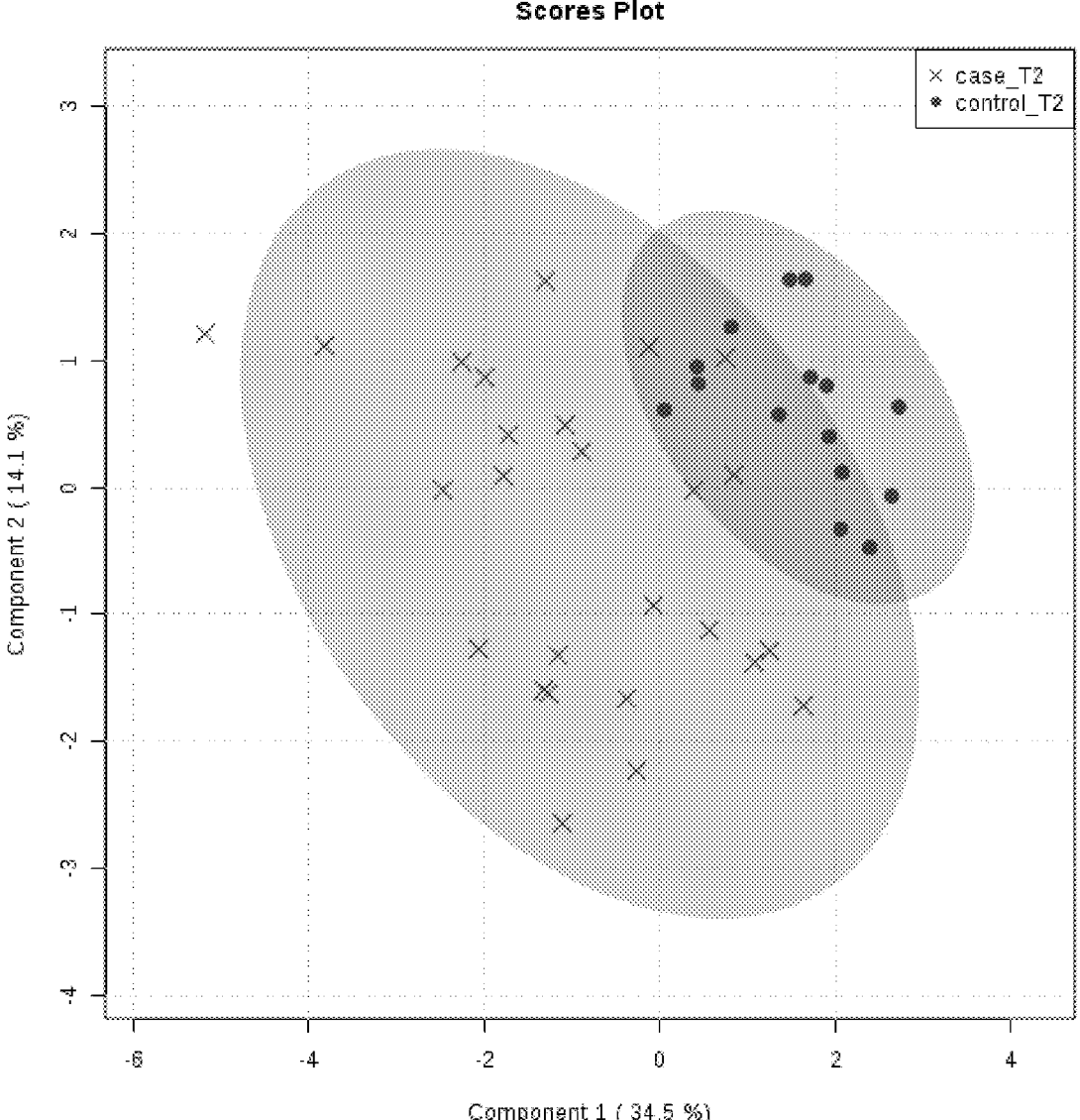
FIGURE 18: PLS-DA plot showing separation between control patients (*blue*) and lung cancer patients (*red*) based on an analysis of serum samples at time T2.

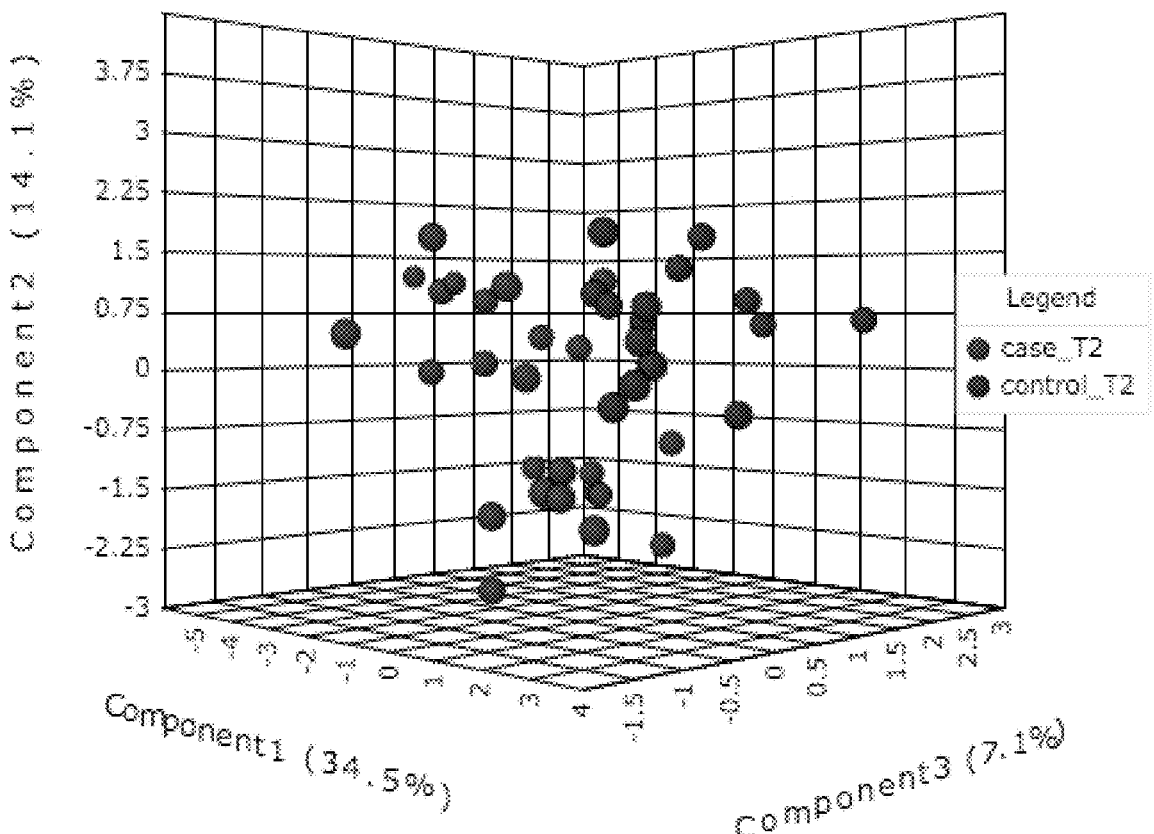
FIGURE 19: PLS-DA plot showing separation between control patients (*blue*) and lung cancer patients (*red*) based on an analysis of serum samples at time T2.

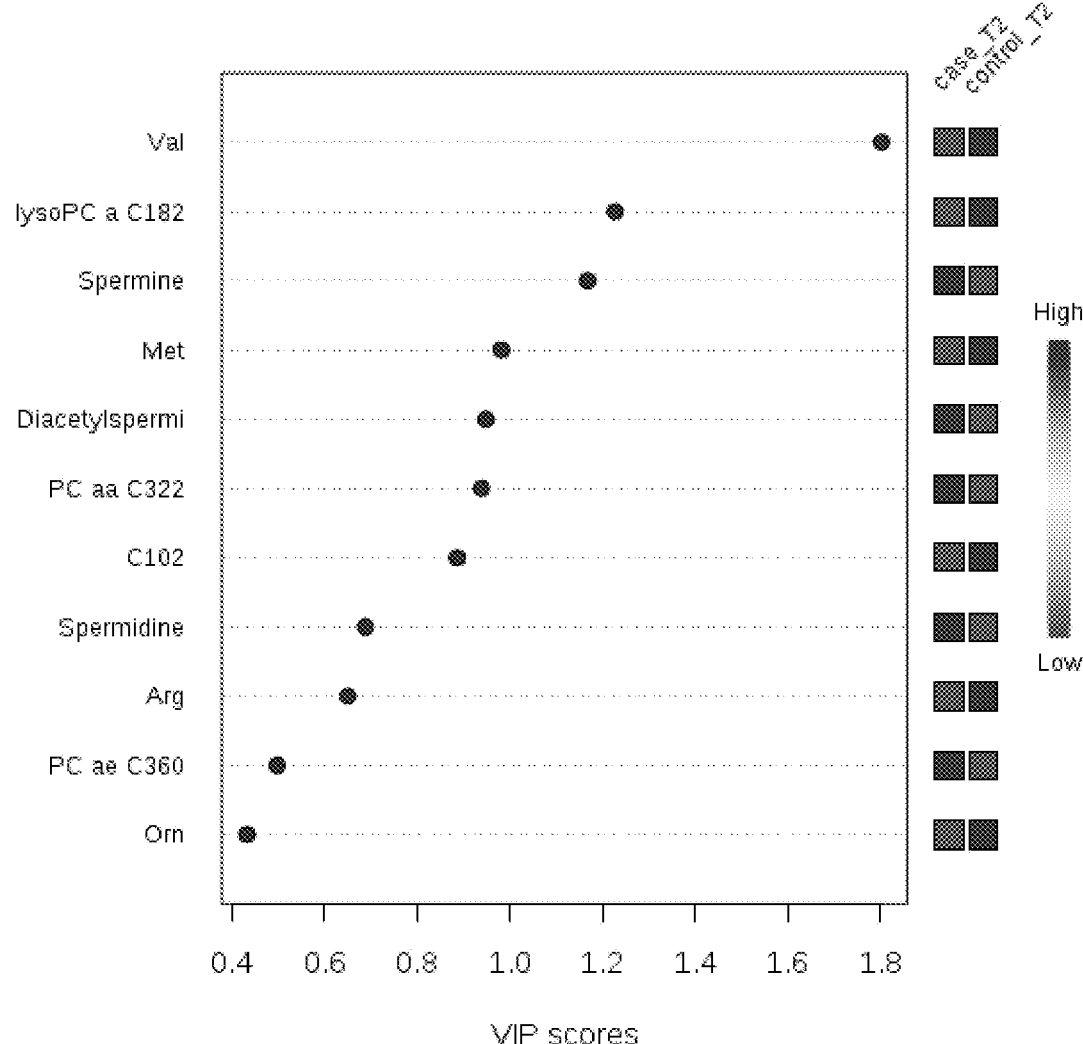
FIGURE 20: VIP analysis plot ranking discriminating serum metabolites in descending order of importance at time T2.

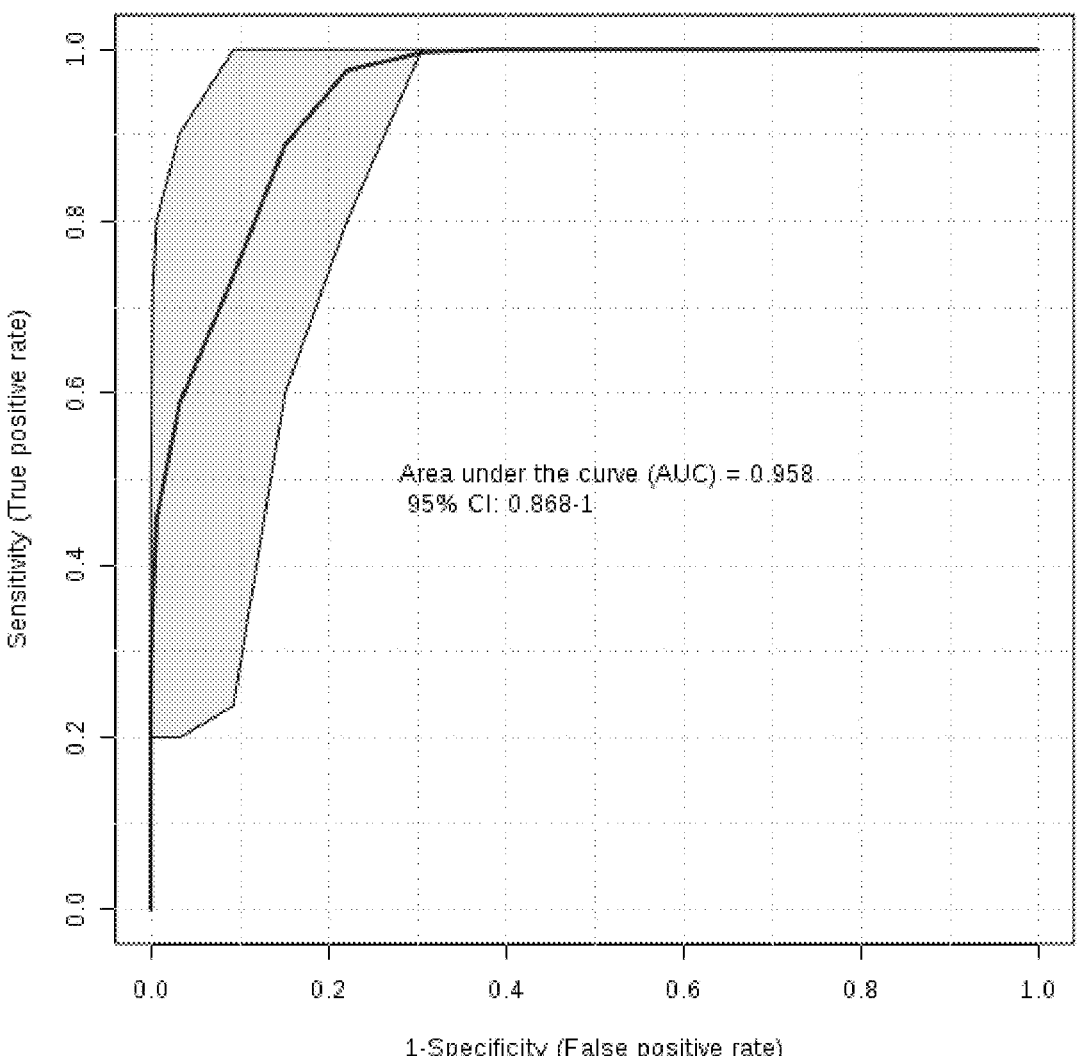
FIGURE 21: ROC analysis including the five most important metabolites from the VIP analysis of serum samples shown in Figure 20.

METHOD OF DETECTING LUNG CANCER

CROSS-REFERENCE TO RELATED APPLICATIONS

This application is a continuation of U.S. Ser. No. 15/739, 608, filed Dec. 22, 2017, which is the U.S. National Stage of and claims priority to International Patent Application No. PCT/CA2016/050758, filed Jun. 27, 2016, entitled METHOD OF DETECTING LUNG CANCER, which claims the priority benefit of U.S. Provisional Application Ser. No. 62/185,213, filed Jun. 26, 2015, entitled METHOD OF DETECTING LUNG CANCER, each of which is incorporated by reference herein in its entirety.

BACKGROUND OF THE INVENTION

Field of the Invention

The present invention relates to a method of detecting cancer and, in particular, to a method of detecting lung cancer by measuring polyamine metabolites and other metabolites.

Description of the Related Art

The polyamine pathway has been demonstrated to be significantly up-regulated in cancer cells. Spermidine/spermine $N^1$-acetyltransferase (SSAT) is recognized as a critical enzyme in the pathway and is highly regulated in all mammalian cells. While SSAT is present in normal tissues in very low concentrations, it is present at much higher levels in cancer cells. Therefore, as cellular levels of SSAT increase, measurement of its enzymatic activity correlates with the presence and severity of cancer.

SUMMARY OF THE INVENTION

There is provided a method of detecting lung cancer by measuring polyamine metabolites and other metabolites in urine and serum.

There is also provided a biomarker panel for a urine test for detecting lung cancer wherein the biomarker panel detects a biomarker selected from the group of biomarkers consisting of DMA, C5:1, C10:1, ADMA, C5-OH, SDMA, and kynurenine, or a combination thereof. The biomarker panel may be used to diagnose lung cancer. The biomarker panel may be used to determine a stage of lung cancer. The biomarker panel may be used to screen for lung cancer. The biomarker panel may be used to determine a treatment prognosis for lung cancer. The biomarker panel may be used to determine efficacy of a drug during the development or clinical phase.

There is further provided a biomarker panel for a serum test for detecting lung cancer wherein the biomarker panel detects a biomarker selected from the group of biomarkers consisting of valine, arginine, ornithine, methionine, spermidine, spermine, diacetylspermine, C10:2, PC aa C32:2, PC ae C36:0, and PC ae C44:5; and lysoPC a C18:2, or a combination thereof. The biomarker panel may be used to diagnose lung cancer. The biomarker panel may be used to determine a stage of lung cancer. The biomarker panel may be used to screen for lung cancer. The biomarker panel may be used to determine a treatment prognosis for lung cancer. The biomarker panel may be used to determine efficacy of a drug during the development or clinical phase.

There is still further provided a biomarker panel for a serum test for detecting lung cancer wherein the biomarker panel detects a biomarker selected from the group of biomarkers consisting of valine, C10:2, PC aa C32:2, PC ae C36:0, PC ae C44:5, or a combination thereof. The biomarker panel may be used to diagnose lung cancer. The biomarker panel may be used to determine a stage of lung cancer. The biomarker panel may be used to screen for lung cancer. The biomarker panel may be used to determine a treatment prognosis for lung cancer. The biomarker panel may be used to determine efficacy of a drug during the development or clinical phase.

There is yet still further provided a panel for a serum test for detecting late stage lung cancer wherein the biomarker panel detects a biomarker selected from the group of biomarkers consisting of valine, diacetylspermine, spermine, C10:2, and lysoPC a C18.2, or a combination thereof. The biomarker panel may be used to diagnose lung cancer. The biomarker panel may be used to determine a stage of lung cancer. The biomarker panel may be used to screen for lung cancer. The biomarker panel may be used to determine a treatment prognosis for lung cancer. The biomarker panel may be used to determine efficacy of a drug during the development or clinical phase.

BRIEF DESCRIPTIONS OF DRAWINGS

The invention will be more readily understood from the following description of the embodiments thereof given, by way of example only, with reference to the accompanying drawings, in which:

FIG. 1 is a box-and-whiskers plot showing the concentrates of metabolites in healthy patients and cancer patients;

FIG. 2 is a partial least squares discriminant analysis (PLS-DA) plot showing separation between control patients and lung cancer patients based on an analysis of urine samples;

FIG. 3 is a variable importance in projection (VIP) analysis plot ranking discriminating urine metabolites in descending order of importance;

FIG. 4 is a receiver operating characteristic (ROC) analysis including the seven most important metabolites from VIP analysis of urine samples shown in FIG. 3;

FIG. 5 is a partial least squares discriminant analysis (PLS-DA) plot showing separation between control patients and lung cancer patients based on an analysis of serum samples;

FIG. 6 is a variable importance in projection (VIP) analysis plot ranking discriminating serum metabolites in descending order of importance;

FIG. 7 is a receiver operating characteristic (ROC) including the five most important metabolites from VIP analysis of serum samples shown in FIG. 6;

FIG. 8 is a table showing a univariate analysis of individual metabolites in serum samples at time T1;

FIG. 9 is a table showing a univariate analysis of individual metabolites in serum samples at time T2;

FIG. 10 is a principal component analysis (PCA) plot showing separation between control patients and lung cancer patients based on an analysis of serum samples at time T1;

FIG. 11 is a three-dimensional principal component analysis (PCA) plot showing separation between control patients and lung cancer patients based on an analysis of serum samples at time T1;

FIG. 12 is a partial least squares discriminant analysis (PLS-DA) plot showing separation between control patients and lung cancer patients based on an analysis of serum samples at time T1;

FIG. 13 is a three-dimensional partial least squares discriminant analysis (PLS-DA) plot showing separation between control patients and lung cancer patients based on an analysis of serum samples at time T1;

FIG. 14 is a variable importance in projection (VIP) analysis plot ranking discriminating serum metabolites in descending order of importance at time T1;

FIG. 15 is a receiver operating characteristic (ROC) analysis including the five most important metabolites from the VIP analysis of serum samples shown in FIG. 14;

FIG. 16 is a principal component analysis (PCA) plot showing separation between control patients and lung cancer patients based on an analysis of serum samples at time T2;

FIG. 17 is a three-dimensional principal component analysis (PCA) plot showing separation between control patients and lung cancer patients based on an analysis of serum samples at time T2;

FIG. 18 is a partial least squares discriminant analysis (PLS-DA) plot showing separation between control patients and lung cancer patients based on an analysis of serum samples at time T2;

FIG. 19 is a three-dimensional partial least squares discriminant analysis (PLS-DA) plot showing separation between control patients and lung cancer patients based on an analysis of serum samples at time T2;

FIG. 20 is a variable importance in projection (VIP) analysis plot ranking discriminating serum metabolites in descending order of importance at time T2; and FIG. 21 is a receiver operating characteristic (ROC) analysis including the five most important metabolites from the VIP analysis of serum samples shown in FIG. 20.

DESCRIPTIONS OF THE PREFERRED EMBODIMENTS

Serum samples from control patients, early stage cancer patients, and late stage cancer patients were analyzed using a combination of direct injection mass spectrometry and reverse-phase LC-MS/MS. An AbsoluteIDQ® p180 Kit obtained from Biocrates Life Sciences AG of Eduard-Bodem-Gasse 8 6020, Innsbruck, Austria was used in combination with an API4000 Qtrap® tandem mass spectrometer obtained from Applied Biosystems/MDS Sciex of 850 Lincoln Centre Drive, Foster City, California, 94404, United States of America, for the targeted identification and quantification of up to 180 different endogenous metabolites including amino acids, acylcarnitines, biogenic amines, glycerophospholipids, sphingolipids and sugars.

The method used combines the derivatization and extraction of analytes, and the selective mass-spectrometric detection using multiple reaction monitoring (MRM) pairs. Isotope-labeled internal standards and other internal standards are integrated in AbsoluteIDQ® p180 Kit plate filter for metabolite quantification. The AbsoluteIDQ® p180 Kit contains a 96 deep-well plate with a filter plate attached with sealing tape as well as reagents and solvents used to prepare the plate assay. First 14 wells in the AbsoluteIDQ® p180 Kit were used for one blank, three zero samples, seven standards and three quality control samples provided with each AbsoluteIDQ® p180 Kit. All the serum samples were analyzed with the AbsoluteIDQ® p180 Kit using the protocol described in the AbsoluteIDQ® p180 Kit User Manual.

Serum samples were thawed on ice and were vortexed and centrifuged at 2750×g for five minutes at 4° C. 10 μL of each serum sample was loaded onto the center of the filter on the upper 96-well kit plate and dried in a stream of nitrogen. 20 μL of a 5% solution of phenyl-isothiocyanate was subsequently added for derivatization. The filter spots were then dried again using an evaporator. Extraction of the metabolites was then achieved by adding 300 μL methanol containing 5 mM ammonium acetate. The extracts were obtained by centrifugation into the lower 96-deep well plate. This was followed by a dilution step with MS running solvent from the AbsoluteIDQ® p180 Kit.

Mass spectrometric analysis was performed on the API4000 Qtrap® tandem mass spectrometer which was equipped with a solvent delivery system. The serum samples were delivered to the mass spectrometer by either a direct injection (DI) method or liquid chromatography method. The Biocrates MetIQ™ software, which is integral to the AbsoluteIDQ® p180 Kit, was used to control the entire assay workflow, from sample registration to automated calculation of metabolite concentrations to the export of data into other data analysis programs. A targeted profiling scheme was used to quantitatively screen for known small molecule metabolites using multiple reaction monitoring, neutral loss, and precursor ion scans.

First Study

Metabolites were detected and quantified in urine samples collected from 10 control patients and 12 lung cancer patients undergoing chemotherapy treatment using LC-MS/MS-based assay. In particular, the following polyamine pathway metabolites: spermidine, spermine, methionine, putrescine, methylthioadenosine (MTA), S-adenosyl-L-methionine (SAMe), ornithine, arginine, N-acetylspermine, and N-acetylspermidine were detected and quantified in urine samples.

The results of this study, shown in FIG. 1, indicate that four metabolites have been identified as putative biomarkers for cancer, namely, spermidine, ornithine, arginine and methionine. The results from this study revealed a preliminary picture of the polyamine metabolome in cancer patients and healthy subjects.

Second Study

Metabolites were detected in urine and serum samples collected from 15 control patients and 31 lung cancer patients (including 7 early stage cancer patients). The samples were analyzed using a combined direct injection mass spectrometry (MS) and reverse-phase LC-MS/MS as described above. Statistical analysis was performed using MetaboAnalyst and ROCCET.

The following metabolites were identified and quantified using the Biocrates Absolute p180IDQ™ Kit:

| Metabolite | Serum | Urine |
|---|---|---|
| Amino Acids | 21 | 21 |
| Acylcarnitines | 23 | 35 |
| Biogenic amines | 13 | 17 |
| Glycerophospholipids (PCs & LysoPCs) | 85 | 32 |
| Sphingolipids | 15 | 6 |
| Hexose | 1 | 1 |

PLS Discriminant Analysis (PLS-DA) resulted in detectable separation of lung cancer patients and control patients based on seven metabolites in urine, as shown in FIG. 2, and five metabolites in serum, as shown in FIG. 5.

Total dimethylarginine in asymmetric and symmetric forms (DMA), tiglylcarnitine (C5:1), decenoylcarnitine (C10:1), asymmetric dimethylarginine (ADMA), hydroxy-valerylcarnitine (C5-OH), symmetric dimethylarginine (SDMA), and kynurenine appear to be the seven most important urinary metabolites for distinguishing lung cancer based on variable importance in projection (VIP) analysis as shown in FIG. 3. A receiver operating characteristic (ROC) analysis including the seven most important metabolites from VIP analysis of urine samples is shown in FIG. 4.

Valine, decadienylcarnitine (C10:2), glycerophosopholipids (PC aa C32:2; PC ae C36:0, and PC ae C44:5) appear to be the five most important serum metabolites for distinguishing lung cancer based on variable importance in projection (VIP) analysis as shown in FIG. 6. A receiver operating characteristic (ROC) analysis including the five most important metabolites from VIP analysis of serum samples is shown in FIG. 7.

Seven putative urinary biomarkers and five putative serum biomarkers have accordingly been identified for diagnosis of lung cancer and may be used in a biomarker panel for a urine test or serum test to detect lung cancer.

Third Study

Metabolites were detected in serum samples collected from 26 late stage lung cancer patients and 15 control patients at times T1 and T2. In particular, the following polyamine pathway metabolites: valine, arginine, ornithine, methionine, spermidine, spermine, diacetylspermine, deca-dienylcarnitine (C10:2), glycerophosopholipids (PC aa C32:2 and PC ae C36:0), lysoPC a C18:2, methylthioad-enosine, and putrescine were detected and quantified in the serum samples at times T1 and T2.

The samples were analyzed using a combined direct injection mass spectrometry (MS) and reverse-phase LC-MS/MS as described above. Statistical analysis was performed using MetaboAnalyst and ROCCET. Methylthioad-enosine and putrescine were however excluded from the analysis because the missing rates were greater than 50%. FIGS. 8 and 9 respectively show the results of a univariate analysis of the remaining individual metabolites at times (T1) and (T2).

Principal component analysis (PCA) and partial least squares discriminant analysis (PLS-DA) at time T1 resulted in a detectable separation of lung cancer patients and control patients based on eleven metabolites in serum as shown in FIGS. 10 to 13.

Total valine, diacetylspermine, spermine, lysoPC a C18.2, and decadienylcarnitine (C10:2) appear to be the five most important serum metabolites for distinguishing late stage lung cancer based on variable importance in projection (VIP) analysis as shown in FIG. 14. A receiver operating characteristic (ROC) analysis including the five most important metabolites from VIP analysis of serum samples is shown in FIG. 15.

Principal component analysis (PCA) and partial least squares discriminant analysis (PLS-DA) at time T2 resulted in a detectable separation of lung cancer patients and control patients based on eleven metabolites in serum as shown in FIGS. 16 to 19.

Total valine, diacetylspermine, spermine, lysoPC a C18.2, and decadienylcarnitine (C10:2) again appear to be the five most important serum metabolites for distinguishing late stage lung cancer based on variable importance in projection (VIP) analysis as shown in FIG. 20. A receiver operating characteristic (ROC) analysis including the five most important metabolites from VIP analysis of serum samples is shown in FIG. 21.

Eleven putative serum biomarkers have accordingly been identified for diagnosis of late stage lung cancer and may be used in a biomarker panel for a serum test to detect lung cancer.

It will be understood by a person skilled in the art that many of the details provided above are by way of example only, and are not intended to limit the scope of the invention which is to be determined with reference to the following claims.

What is claimed:

1. A method for processing a human clinical urine sample, the method comprising obtaining a urine sample from a subject clinically assessed as having or suspected of having lung cancer, and quantifying a panel of metabolites in said urine sample, the panel comprising at least one urinary metabolite selected from C5:1, C10:1, ADMA, C5-OH, and SDMA.

2. The method of claim 1, wherein the panel comprises at least two of said urinary metabolites.

3. The method of claim 1, wherein the panel comprises at least three of said urinary metabolites.

4. The method of claim 1, wherein the at least one urinary metabolite comprises C5:1.

5. The method of claim 1, wherein the at least one urinary metabolite comprises C10:1.

6. The method of claim 1, wherein the at least one urinary metabolite comprises ADMA.

7. The method of claim 1, wherein the at least one urinary metabolite comprises C5-OH.

8. The method of claim 1, wherein the at least one urinary metabolite comprises SDMA.

9. The method of claim 1, wherein the panel of metabolites further comprises at least one further urinary metabolite selected from DMA and kynurenine.

10. The method of claim 9, wherein the at least one further urinary metabolite comprises DMA.

11. The method of claim 9, wherein the at least one further urinary metabolite comprises kynurenine.

12. The method of claim 1, wherein the panel of metabolites further comprises at least one further urinary metabolite selected from spermidine, ornithine, arginine, and methio-nine.

* * * * *